US00PP12526P2

(12) United States Plant Patent
Vandenberg et al.

(10) Patent No.: US PP12,526 P2
(45) Date of Patent: Apr. 9, 2002

(54) CHRYSANTHEMUM PLANT NAMED 'YOAUBURN'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 15 days.

(21) Appl. No.: 09/594,751

(22) Filed: Jun. 16, 2000

(51) Int. Cl.[7] ..... A01H 5/00
(52) U.S. Cl. ..... Plt./296

(58) Field of Search ..... Plt./286, 296

*Primary Examiner*—Howard J. Locker
(74) *Attorney, Agent, or Firm*—C. A. Whealy

(57) ABSTRACT

A distinct cultivar of Chrysanthemum plant named 'Yoauburn', characterized by its upright, outwardly spreading and uniformly mounded plant habit; very freely branching habit; uniform flowering response; early flowering, eight-week response time; floriferousness; daisy-type inflorescences that are about 7.2 cm in diameter; orange bronze-colored ray florets and bright yellow disc florets; excellent ray floret color retention; good performance under winter conditions; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yoauburn.

The new Chrysanthemum is a product of a planned breeding program conducted by the Inventors in Salinas, Calif. and Fort Myers, Fla. The objective of the breeding program is to create new potted Chrysanthemum cultivars with desirable inflorescence form and floret colors and good postproduction longevity.

The new Chrysanthemum originated from a cross made by the Inventors in October, 1994, in Salinas, Calif., of a proprietary Chrysanthemum seedling selection identified as YB-4439 as the female, or seed, parent with a proprietary Chrysanthemum seedling selection identified as YB-6616 as the male, or pollen, parent. The new Chrysanthemum was discovered and selected by the Inventors in November, 1996, as a single flowering plant within the progeny of the stated cross grown in a controlled environment in Fort Myers, Fla. The selection of this plant was based on its desirable inflorescence form and floret colors and good postproduction longevity.

Asexual reproduction of the new Chrysanthemum by vegetative tip cuttings was first conducted in Fort Myers, Fla. in January, 1997. Asexual reproduction by cuttings has shown that the unique features of this new Chrysanthemum are stable and reproduced true to type in successive generations.

SUMMARY OF THE INVENTION

The cultivar Yoauburn has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoauburn'. These characteristics in combination distinguish 'Yoauburn' as a new and distinct Chrysanthemum:

1. Upright, outwardly spreading and uniformly mounded plant habit.
2. Very freely branching, dense and full plants.
3. Uniform flowering response.
4. Early flowering, eight-week response time.
5. Very freely flowering.
6. Daisy-type inflorescences that are about 7.2 cm in diameter.
7. Orange bronze-colored ray florets and bright yellow disc florets.
8. Excellent ray floret color retention.
9. Can be grown as a natural spray-type.
10. Good performance under winter conditions.
11. Good postproduction longevity with inflorescences maintaining good substance and color for about three weeks in an interior environment.

Plants of the new Chrysanthemum differ from plants of the cultivar, Orange Davis, disclosed in U.S. Plant Pat. No. 8,295, in the following characteristics:

1. Plants of the new Chrysanthemum are not as outwardly spreading as plants of the cultivar Orange Davis.
2. Plants of the new Chrysanthemum and plants of the cultivar Orange Davis differ in ray floret color.
3. Plants of the new Chrysanthemum flower more uniformly than plants of the cultivar Orange Davis.
4. Plants of the new Chrysanthemum flower about 4 to 6 days earlier than plants of the cultivar Orange Davis.
5. Under high production temperatures, ray florets of plants of the new Chrysanthemum do not exhibit floret color break (yellow flecking on ray florets) whereas ray florets of plants of the cultivar Orange Davis will exhibit floret color break.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yoauburn'.

The photograph at the bottom of the sheet comprises a close-up view of typical inflorescences of the cultivar Yoauburn.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yoauburn.

Commercial classification: Daisy-type potted Chrysanthemum.

Parentage:

*Female, or seed parent.*—Proprietary Chrysanthemum seedling selection identified as YB-4439.

*Male, or pollen, parent.*—Proprietary Chrysanthemum seedling selection identified as YB-6616.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy-type potted Chrysanthemum which can be grown as a natural spray-type. Inverted triangle; stems upright and outwardly spreading giving a uniformly mounded appearance to the plant. Very freely branching, about four or five lateral branches develop after removal of terminal apex (pinching); dense and full plants. Moderate to high vigor.

*Plant height.*—About 28 cm.

*Plant width.*—About 45 cm.

*Lateral branches.*—Length: About 20.5 cm. Diameter: About 3.5 mm. Internode length: About 2.1 cm. Strength: Strong. Texture: Pubescent. Color: 144A.

*Foliage description.*—Arrangement: Alternate. Length: About 5.25 cm. Width: About 4.3 cm. Apex: Cuspidate. Base: Mostly truncate. Margin: Palmately lobed, sinuses between lateral lobes divergent to convergent. Texture: Upper and lower surfaces with very fine pubescence; veins prominent on lower surface. Color: Young foliage upper surface: 147A. Young foliage lower surface: Darker than 147B. Mature foliage upper surface: 147A. Mature foliage lower surface: 147B. Venation upper surface: 147A to 147B. Venation lower surface: 147B. Petiole length: About 2.4 cm. Petiole diameter: About 3 mm. Petiole color: 147A to 147B.

Inflorescence description:

*Appearance.*—Daisy-type inflorescence form with elongated oblong-shaped ray florets. Inflorescences borne on terminals above foliage, Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Typically grown as a spray-type; about six inflorescences per lateral stem, about 24 to 30 inflorescences per plant.

*Inflorescence bud.*—Height: About 6 mm. Diameter: About 8.5 mm. Color: 143A to 137A.

*Inflorescence size.*—Diameter: About 7.2 cm. Depth (height): About 2.2 cm. Diameter of disc: About 1.4 cm. Receptacle diameter: About 5 mm.

*Ray florets.*—Shape: Elongated-oblong. Orientation: Somewhat upright, about 25 to 30° from perpendicular to peduncle. Aspect: Straight with slight recurve at apex. Length: About 3.4 cm. Width: About 1.2 cm. Apex: Acute, emarginate or dentate. Base: Attenuate; short corolla tube. Margin: Entire. Texture: Smooth, glabrous, satiny. Number of ray florets per inflorescence: About 29; three rows. Color: When opening, upper surface: Close to 10A to 11A overlain with red, 45A to 46A. When opening, lower surface: Close to 10A to 11A with faint undertones of 45A and 46A from upper surface. Fully opened, upper surface: Close to 10A to 11A, overlain with red, 45A and 46A, red most intense as longitudinal stripes, at margins and apex. Overall tonality, darker than 163A to 167A or slightly more yellow than 167A; overall tonality fading to 163A to 163B with subsequent development. Fully opened, lower surface: Close to 10A to 11A with faint undertones of 45A and 46A from upper surface. Overall tonality, close to 164C.

*Disc florets.*—Shape: Tubular, elongated. Apex: Five-pointed. Length: About 6 mm. Width: Apex, about 1.5 mm; base, about 1 mm. Number of disc florets per inflorescence: About 75. Color: Immature: 144A. Mature: Apex: 9A. Mid-section: 154C to 154D. Base: 155D.

*Peduncles.*—Length: First peduncle: About 3.8 cm. Fourth peduncle: About 6.3 cm. Diameter: About 2.5 mm. Angle to vertical: Wide, about 55 to 60° from vertical. Strength: Strong, wiry, flexible. Color: 144A.

*Reproductive organs.*—Androecium: Present on disc florets only. Anther color: 9A. Pollen amount: Scarce to moderate. Pollen color: 14A to 15A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yoauburn', as illustrated and described.

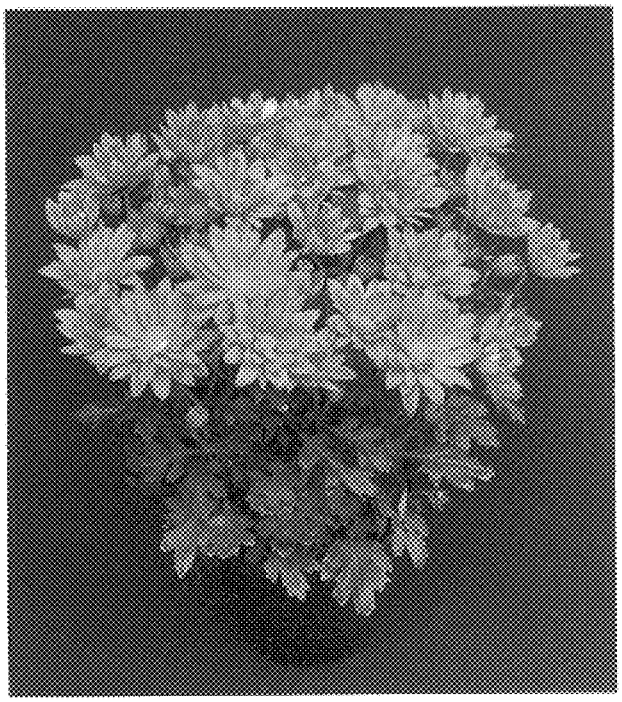
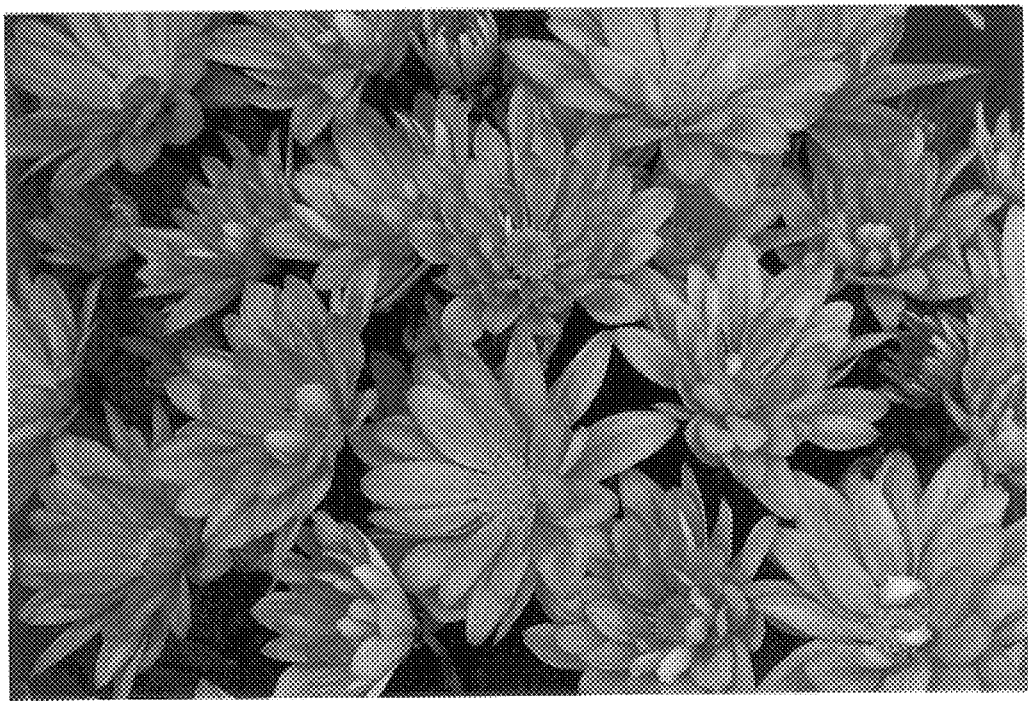

* * * * *